(12) United States Patent
Cioanta et al.

(10) Patent No.: US 8,728,809 B2
(45) Date of Patent: May 20, 2014

(54) USE OF PRESSURE WAVES FOR STIMULATION, PROLIFERATION, DIFFERENTIATION AND POST-IMPLANTATION VIABILITY OF STEM CELLS

(75) Inventors: Iulian Cioanta, Duluth, GA (US); Christopher M. Cashman, Duluth, GA (US)

(73) Assignee: Sanuwave, Inc., Alpharetta, GA (US)

( * ) Notice: Subject to any disclaimer, the term of this patent is extended or adjusted under 35 U.S.C. 154(b) by 321 days.

(21) Appl. No.: 12/900,818

(22) Filed: Oct. 8, 2010

(65) Prior Publication Data
US 2011/0087157 A1 Apr. 14, 2011

Related U.S. Application Data

(60) Provisional application No. 61/249,928, filed on Oct. 8, 2009.

(51) Int. Cl.
*C12N 5/074* (2010.01)

(52) U.S. Cl.
USPC .............................. 435/366; 601/2

(58) Field of Classification Search
None
See application file for complete search history.

(56) References Cited

U.S. PATENT DOCUMENTS

| 2007/0065420 | A1* | 3/2007 | Johnson | 424/93.7 |
| 2007/0249046 | A1* | 10/2007 | Shields | 435/366 |
| 2008/0045882 | A1* | 2/2008 | Finsterwald | 604/22 |

OTHER PUBLICATIONS

Yang, C., et al., "The Effect of High Energy Shock Waves (HESW) on Human Bone Marrow," Urological Research, 1988, pp. 427-429, vol. 16, Issue 6, Springer-Verlag Berlin, Germany.
Critchlow, Matthew A., et al., "The effects of age on the response of rabbit periosteal osteogrogenitor cells to exogenous transforming growth factor-beta2," Journal of Cell Science, 1994, pp. 499-516, vol. 107, The Company of Biologists Limited, United Kingdom.
O'Driscoll, S.W., et al., "Chondrogenesis in periosteal explants. An organ culture model for in vitro study," The Journal of Bone and Joint Surgery, Jul. 1994, pp. 1042-1051, vol. 76-A, No. 7, The Journal of Bone and Joint Surgery, Needham, Massachusetts.
Delius, M., et al., "Biological effects of shock waves: in vivo effect of high energy pulses on rabbit bone." Ultrasound in Medicine & Biology, 1995, pp. 1219-1225, vol. 21, No. 9, Pergamon Press, United Kingdom.
Uslu, M.M., et al., "The effect of extracorporeal shock wave treatment (ESWT) on bone defects. An experimental study," Bulletin (Hospital for Joint Diseases (New York, N.Y.)), 1999, pp. 114-118, vol. 58, No. 2, Hospital for Joint Diseases, New York, New York.
Vaeterlein, N., et al., "The effect of extracorporeal shock waves on joint cartilage—an in vivo study in rabbits," Archives of Orthopaedic and Trauma Surgery, 2000, pp. 403-406, vol. 120, Springer-Verlag Berlin, Germany.
Gahrton, G., et al., "Progress in haematopoietic stem cell transplantation for multiple myeloma," Journal of Internal Medicine, Sep. 2000, pp. 185-201, vol. 248, No. 3, Blackwell Scientific Publications, United Kingdom.
Wang, Feng-Sheng, et al., "Physical Shock Wave Mediates Membrane Hyperpolarization and Ras Activation for Osteogenesis in Human Bone Marrow Stromal Cells," Biochemical and Biophysical Research Communications, 2001, pp. 648-655, vol. 287, No. 3, Academic Press, New York, New York.
Ohtori, Seiji, et al., "Shock wave application to rat skin induces degeneration and reinnervation of sensory nerve fibres," Neuroscience Letters, 2001, pp. 57-60, vol. 315, Elsevier Science Ireland Ltd., Ireland.
Wang, Feng-Sheng, et al., "Superoxide Mediates Shock Wave Induction of ERK-dependent Osteogenic Transcription Factor (CBFA1) and Mesenchymal Cell Differentiation toward Osteoprogenitors," The Journal of Biological Chemistry, Mar. 29, 2002, pp. 10931-10937, vol. 277, No. 13, The American Society for Biochemistry and Molecular Biology, Inc., Baltimore, Maryland.
Wang, F.S., et al., "Extracorporeal shock wave promotes growth and differentiation of bone-marrow stromal cells towards osteoprogenitors associated with induction of TGF-beta1," The Journal of Bone and Joint Surgery (British), Apr. 2002, pp. 457-461, vol. 84-B, No. 3, British Editorial Society of Bone and Joint Surgery, United Kingdom.
Tischer, T., et al, "Extracorporeal shock waves induce ventral-periosteal new bone formation out of the focus zone—results of an in-vivo animal trial," May-Jun. 2002, pp. 281-285, vol. 140, No. 3, Zeitschrift für Orthopädie und ihre Grenzgebiete, Ferdinand Enke Verlag, Germany.
Simon, Timothy M., et al., "Cambium cell stimulation from surgical release of the periosteum," Journal of Orthopaedic Research, 2003, pp. 470-480, vol. 21, Elsevier Science Ltd., United States.
Suzuki, H., et al., "Effect of Shock Wave on the Catalytic Activity of Endothelial Nitric Oxide Synthase in Human Umbilical Vein Endothelial Cells," 6th International Congress of the International Society for Medical Shockwave Treatment (www.ismst.com), 2003, International Society for Medical Shockwave Treatment, Austria.
Dorotka, R., et al., "Effects of extracorporeal shock waves on human articular chondrocytes and ovine bone marrow stromal cells in vitro," Archives of Orthopaedic and Trauma Surgery, Sep. 2003, pp. 345-348, vol. 123, No. 7, Springer Berlin, Germany.
Chen, Yeung-Jen, et al., "Recruitment of mesenchymal stem cells and expressio of TGF-beta1 and VEGF in the early stage of shock wave-promoted bone regeneration of segmented defect in rats," Journal of Orthopaedic Research, May 2004, pp. 526-534, vol. 22, Issue 3, John Wiley & Sons, Inc., Hoboken, New Jersey.

(Continued)

*Primary Examiner* — Allison Ford
*Assistant Examiner* — Yvonne Pyla
(74) *Attorney, Agent, or Firm* — Hunton & Williams LLP

(57) ABSTRACT

Stem cells are proliferated with the application of acoustic pressure waves, including cambium cells of periosteum treated in-vivo with acoustic pressure waves. Following harvesting and viability assessment of in-vivo or in-vitro proliferated stem cells, acoustic pressure waves are applied to enhance in-vivo or in-vitro differentiation either before or after implantation of the stems cells to an organism. Acoustic pressure waves also stimulate an implantation site to enhance viability and to grow desired tissue.

14 Claims, 3 Drawing Sheets

(56) References Cited

OTHER PUBLICATIONS

Wang, Feng-Sheng, et al., "Shockwave Stimulates Oxygen Radical-Mediated Osteogenesis of the Mesenchymal Cells From Human Umbilical Cord Blood," Journal of Bone and Mineral Research, Jun. 2004, pp. 973-982, vol. 19, No. 6, John Wiley & Sons, Inc., Hoboken, New Jersey.

Chen, Yeung-Jen, et al., "Activation of extracellular signal-regulated kinase (ERK) and p38 kinase in shock wave-promoted bone formation of segmental defect in rats," Bone, Mar. 2004, pp. 466-477, vol. 34, Issue 3, Elsevier Inc., United States.

Takahashi, K., et al. "Gene Expression for Extracellular Matrix Proteins in Shockwave-Induced Osteogenesis in Rats," Calcified Tissue International, Apr. 2004, pp. 187-193, vol. 74, No. 2, Springer-Verlag New York Inc., New York, New York.

Maier, M., et al., "New bone formation by extracorporeal shock waves. Dependence of induction on energy flux density," Der Orthopaede, Dec. 2004, pp. 1401-1410, vol. 33, No. 12, Springer-Velag Berlin, Germany.

Tam, K.F., et al., "Delayed stimulatory effect of low-intensity shockwaves on human periosteal cells," Clinical Orthopaedics and Related Research, Sep. 2005, pp. 260-265, vol. 438, Springer, New York, New York.

Mardones, Rodrigo M., et al., "Development of a Biologic Prosthetic Composite for Cartilage Repair," Tissue Engineering, Sep.-Oct. 2005, pp. 1368-1378, vol. 11, No. 9/10, Mary Ann Liebert, Inc., New York, New York.

Takahashi, Norimasa, et al., "Second Application of Low-energy Shock Waves Has a Cumulative Effect on Free Nerve Endings," Clinical Orthopaedics and Related Research, Feb. 2006, pp. 315-319, vol. 438, Springer, New York, New York.

Martini, Lucia, et al., "Early Effects of Extracorporeal Shock Wave Treatment on Osteoblast-like Cells: A Comparative Study Between Electromagnetic and Electrohydraulic Devices," The Journal of Trauma, Nov. 2006, pp. 1198-1206, vol. 61, No. 5, Lippincott Williams & Wilkins, Baltimore, Maryland.

Alexander, Dorothea, et al., "Jaw periosteal cells: a suitable source for mesenchymal stem cells?" European Cells and Materials, 2007, p. 48, vol. 14, Supplement 1, AO Foundation, Switzerland.

Moretti, Biagio, et al., "Osteoblast repair action induced by ESWT," 11th International Congress of the International Society for Medical Shockwave Treatment (www.ismst.com), 2008, Abstract No. 54, International Society for Medical Shockwave Treatment, Austria.

Neuland, Helmut Garrelt, et al., "Focused Extracorporeal Shock Waves Influence Migration, Proliferation and Growth of Human Mesenchymal Stem Cells," 11th International Congress of the International Society for Medical Shockwave Treatment (www.ismst.com), 2008, Abstract No. 55, International Society for Medical Shockwave Treatment, Austria.

Delhasse, Yvonne, et al., "Comparative study between the effects and mode of application of focused and radial shock wave treatment on the behaviour of human mesenchymal stem cells (MSC)," 11th International Congress of the International Society for Medical Shockwave Treatment (www.ismst.com), 2008, Abstract No. 57, International Society for Medical Shockwave Treatment, Austria.

Morton, Tatjana J., et al., "Shockwave therapy on human fat-derived stem cells," 11th International Congress of the International Society for Medical Shockwave Treatment (www.ismst.com), 2008, Abstract No. 57, International Society for Medical Shockwave Treatment, Austria.

Yip, Hon-Kan, et al., "Shock Wave Therapy Applied to Rat Bone Marrow-Derived Mononuclear Cells Enhances Formation of Cells Stained Positive for CD31 and Vascular Endothelial Growth Factor," Circulation Journal, Jan. 2008, pp. 150-156, vol. 72, No. 1, Japanese Circulation Society, Japan.

Ringe, J., et al., "Human mastoid periosteum-derived stem cells: promising candidates for skeletal tissue engineering," Journal of Tissue Engineering and Regenerative Medicine, Mar.-Apr. 2008, pp. 136-146, vol. 2, No. 2-3, John Wiley & Sons, United Kingdom.

Kane, Ed, "Stem-cell therapy shows promise for horse soft-tissue injury, diseases," DVM Newsmagazine (http://veterinarynews.dvm360.com), May 1, 2008, Advanstar Communications, Inc., Lenexa, Kansas.

Siemionow, Maria, et al., "Influence of Pulsed Acoustic Cellular Therapy on Cremaster Muscle Flap Microcirculation and Cellular Interactions Involved in Wound Healing," Third Congress of the World Union of Wound Healing Societies (www.wuwhs.com), Jun. 2008, Abstract No. PF352, World Union of Wound Healing Societies.

Tischer, T., et al, "Dose-Dependent New Bone Formation by Extracorporeal Shock Wave Application on the Intact Femur of Rabbits," European Surgical Research, Jul. 2008, pp. 44-53, vol. 41, No. 1, S. Karger AG, Switzerland.

Reinholz, Gregory G., et al., "Rejuvenation of Periosteum for Tissue Engineering using Local Growth Factor Injection," 54th Annual Meeting of the Orthopaedic Research Society (www.ors.org), 2008, Paper No. 0587, Transactions vol. 33, Orthopaedic Research Society, Rosemont, Illinois.

Neuland, Helmut G., et al., "Focused and Radial Shock Wave Treatment Influence Human Mesenchymal Stem Cells," 12th International Congress of the International Society for Medical Shockwave Treatment (www.ismst.com), 2009, Abstract No. 6, International Society for Medical Shockwave Treatment, Austria.

Vigato, Enrico, et al., "The Effect of Shock Waves on Differentiation and Function of Myofibroblast," 12th International Congress of the International Society for Medical Shockwave Treatment (www.ismst.com), 2009, Abstract No. 9, International Society for Medical Shockwave Treatment, Austria.

* cited by examiner

USE OF PRESSURE WAVES FOR STIMULATION, PROLIFERATION, DIFFERENTIATION AND POST-IMPLANTATION VIABILITY OF STEM CELLS

CROSS-REFERENCE TO RELATED APPLICATIONS

The present application claims the benefit of priority of U.S. Provisional Application No. 61/249,928 filed Oct. 8, 2009, which is incorporated herein by reference.

BACKGROUND OF THE INVENTION

Scientists primarily work with two kinds of stem cells from animals and humans, respectively "embryonic stem cells" and non-embryonic "somatic" or "adult stem cells". There is a third category called "induced pluripotent stem cells" that can be generated under special conditions, which allow some specialized adult cells to be "reprogrammed" genetically to assume a stem cell-like state.

Medical researchers believe that stem cell therapy has the potential to dramatically change the treatment of human disease. A number of adult stem cell therapies already exist, particularly bone marrow transplants that are used to treat leukemia. It is anticipated that in the future, stem cell will be used to treat a wider variety of diseases including cancer, Parkinson's disease, spinal cord injuries, Amyotrophic lateral sclerosis, multiple sclerosis, muscle and bone damage, vision and hearing loss, and diabetes, amongst a number of other impairments and conditions. Scientists are already using stem cells in the laboratory to screen new drugs and to develop model systems to study normal growth and identify the causes of birth defects. Finally, research on stem cells continues to advance knowledge about how an organism develops from a single cell and how healthy cells replace damaged cells in adult organisms.

The adult stem cells have less legal, humanitarian and body rejection hurdles, when compared with embryonic stem cells, which makes them more attractive for the stem cells treatments. Unfortunately, there are reduced numbers of stem cells viable for multiplication and differentiation, when compared to the embryonic stem cells. There is therefore a need for stem cell harvesting to be made more efficient, including maximizing the number of cells harvested from one site. There is a further need for improving the efficiency and potentially successful outcome in post-harvest stem cell treatment steps, such as proliferation of viable stem cells sufficient for tissue generation, differentiation to desired cell types, maintaining survival of the cells in a transplant recipient, and integrating with desired tissue and with proper function in a recipient.

SUMMARY OF THE INVENTION

Acoustic pressure waves are used in embodiments of the invention to stimulate the body to grow more potent and viable cells at the donor site, before the harvesting. In one embodiment a thickening of the periosteum, including the cambium layer, is provided by application of extracorporeal shock/pressure waves (ESPW) that results in periosteal osteogenesis.

In another embodiment, a sufficient number and energy of acoustic pressure waves are applied to target stem cells to in-vivo or in-vitro proliferate stems cells and the proliferated stem cells are transplanted by at least one of autologous transplant and allogenic transplant to a targeted tissue for treatment and subsequently a sufficient number and energy of acoustic pressure waves is applied to the transplant site to stimulate reconstruction of the targeted tissue.

In another embodiment, a sufficient number and energy of acoustic pressure waves are applied to target stem cells that are harvested in-vivo in order to proliferate stems cells in an in-vitro environment and the proliferated stem cells are transplanted by at least one of autologous transplant and allogenic transplant to a targeted tissue for treatment and subsequently a sufficient number and energy of acoustic pressure waves is applied to the transplant site to stimulate reconstruction of the targeted tissue.

In still further embodiments, acoustic pressure waves are applied in sufficient number and energy to proliferated cells (whether proliferated in-vivo or in-vitro) to stimulate differentiation before they are transplanted by at least one of autologous transplant and allogenic transplant to a targeted tissue for treatment and subsequently a sufficient number and energy of acoustic pressure waves is applied to the transplant site to stimulate reconstruction of the targeted tissue.

In one embodiment, acoustic pressure waves are applied to stem cells in a container and under ambient pressure, such as from 1 to 3 bars, to stimulate differentiation.

In further embodiments, a target tissue site for implantation of stem cells or tissue is pre-conditioned with applied acoustic pressure waves to improve the viability and outcome of the stem cell or tissue implantation. In one embodiment acoustic pressure waves are subsequently applied to the implant site of the stem cells or tissue.

DETAILED DESCRIPTION OF THE INVENTION

Figure 1A:
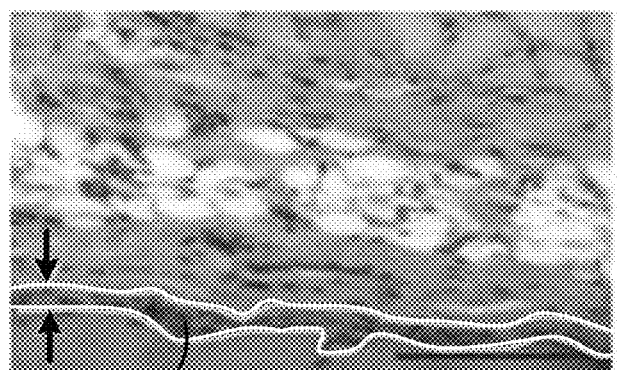
FIG. 1A is a photograph of a cambium layer of an adult rat periosteum prior to application of acoustic pressure waves according to one embodiment of the present invention.

In embodiments of the invention, extracorporeal shock/pressure waves (ESPW) can produce periosteal osteogenesis with thickening of the cambium layer.

Example 1

Thirteen (13) rats were used in this example, divided into two groups: Group 1 consisted of 5 male Sprague-Dawley rats aged 4 months and weighing 400-450 g. Rats were anaesthetized using 2% isoflourane and placed in the prone position in preparation for the shockwave treatment. The rat was shaved in the treatment area prior to application of the shock/pressure waves and ultrasound gel was used as a coupling medium between the shock wave device and the animal. An electrohydraulic shockwave/pressure waves source (Ossatron device of Sanuwave, Inc., Marietta, Ga.)) was used at 0.42 mJ/mm$^2$ (energy flux density), for 3000 impulses at 4 Hz. The device was oriented such that the shockwave source was positioned on the lateral side of the femur with the center of the focal zone 2 cm distal to the hip joint. Rats were sacrificed 4 days post treatment and the femurs and surrounding soft tissue were fixed in formalin, decalcified, and embedded in paraffin. Contralateral femurs were used as controls. Group 2 consisted of 8 female Lewis rats aged 12 weeks and weighing 185-195 g. Rats were anaesthetized, prepared and positioned as described above. This group underwent 3 sessions at 1 wk intervals but a lower energy and smaller focal zone electrohydraulic shockwave/pressure waves device was used (EvoTron device of SANUWAVE, Inc. (Marietta, Ga.)). Each session consisted of 1000 shocks at 0.15 mJ/mm$^2$ and 4 Hz. Rats were sacrificed 7 days post treatment and the femurs and surrounding tissues processed for histology as above, with the contralateral limbs used as controls.

Figure 1B:
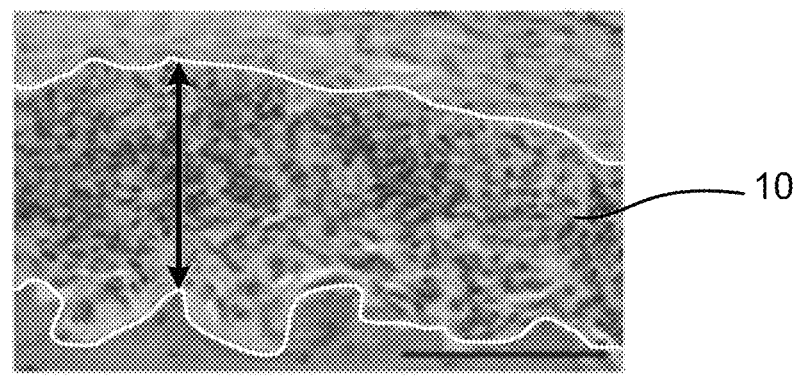
FIG. 1B is a photograph of a cambium layer of the adult rat periosteum of FIG. 1A after application of acoustic pressure waves according to one embodiment of the present invention.

Histomorphometric analysis was performed on H&E slides from the Group 1 femurs by counting the number of the cambium cells ("cell counts") at 8 positions around the circumference of the bone in an area 50 μm wide through the entire thickness of the cambium layer, distinguished morphologically from the overlying fibrous tissue layer. Referring to FIGS. 1A and 1B, the ESPW-treated limbs of Group 1 rats displayed a significant (3-fold) increase in the number of cambium cells compared to controls (47±4 cells vs. 15±1; mean±SEM; n=40 positions; t-test, p<0.001). Within the group of five animals, three of the treated limbs showed a dramatic thickening of the periosteal cambium layer 10 (cell count=64±3; n=24); two of the treated limbs had a less dramatic thickening (cell count=23±1; n=16). The cell density in the cambium layer 10 of the shocked limbs was equivalent to the control samples. Referring to FIGS. 1A and 1B, the increased cell numbers resulted from a thickened cambium layer 10.

Micrographs of periosteum from FIGS. 1A and 1B show for Group 1 rats 4 days post-ESPW treatment. FIG. 1A represents the contralateral control and FIG. 1B the ESPW sample. The proliferative effect of ESPW on the cambium layer 10 cells of the periosteum is clearly seen (light gray outlines and arrows). Scale bar is 100 μm.

Figure 2:
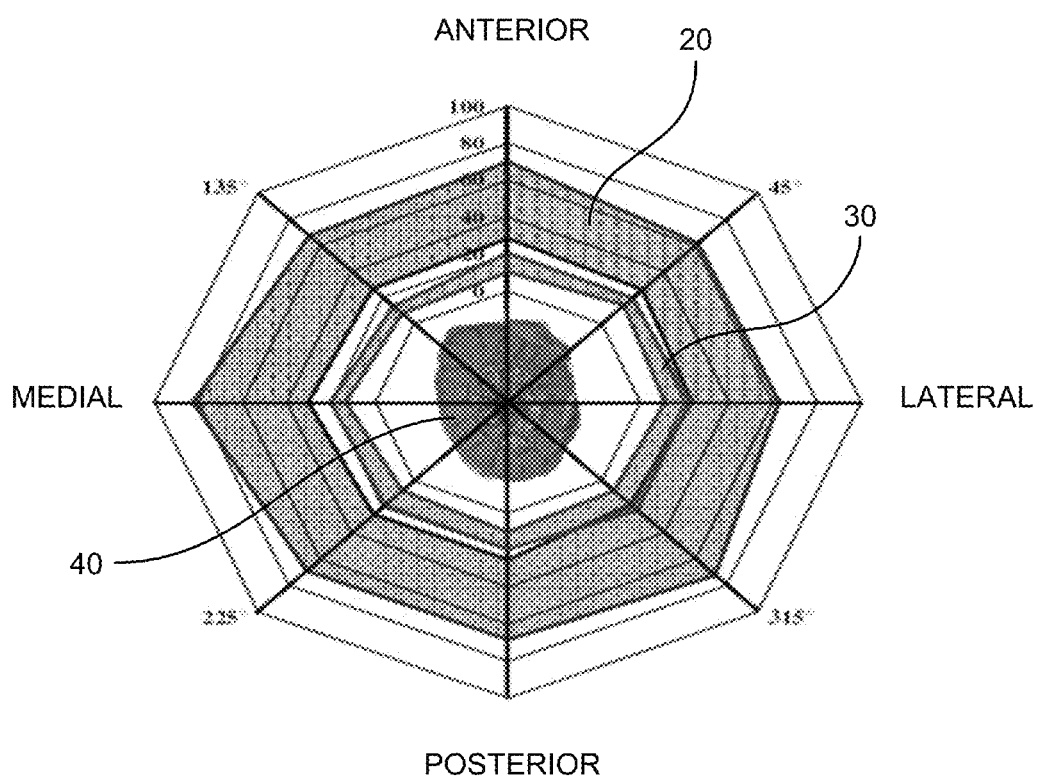
FIG. 2 is a comparison graph of confidence intervals (95%) of periosteal cell counts at eight positions around the circumference of acoustic pressure wave-treated femur bone (outer band) and untreated, control femur bone (inner band) including an inset of a typical histological micrograph of a rat femur cross-section according to one embodiment of the present invention.

Mitotic figures were seen in cambium layer 10 cells of all Group 1 shocked samples. Osteogenesis was initiated in just 4 days in the treated limbs, with small areas of periosteal immature woven bone (ranging from 30 μm×30 μm to 140 μm×80 μm) found in the three samples with more pronounced thickening of the periosteum. The newly formed bone regions were most prominent on the medial side but were found at all positions around the circumference. The 5 shocked rats demonstrated variable hemorrhage and inflammation in the soft tissue. Referring to FIG. 2, two-factor ANOVA showed a significant effect of shock versus control (p<0.0001), but no effect of anatomic position, on cambium cell counts.

The graph of confidence intervals (95%) presented in FIG. 2 for Group 1 periosteal cell counts at eight positions around the circumference of the bone for the shock wave treated 20 and control 30 groups (n=5). Inset 40 shows typical histological micrograph of femur cross-section.

For the animals in Group 2, the H&E stained slides showed two of the treated limbs with a markedly thickened periosteum primarily in the region between the medial and posterior sides. The other 6 samples did not show an obvious periosteal thickening. However, there was evidence of periosteal bone growth on the medial side of all six samples.

The results of this investigation show that ESPW can be employed in embodiments of the invention for thickening of the periosteal cambium cell layer 10. All samples in Group 1 showed significant periosteal thickening after only 4 days post-ESPW treatment.

Due to the ESPW treatment the number of cambium cells in the femur and tibia increased 3- to 6-fold, respectively, 4 days post-treatment with 3,000 shocks at 0.42 mJ/mm$^2$, and there was an almost 10-fold increase in the thickness of the ESPW-stimulated periosteum compared to the anatomic control. In the tibia, the high dose of ESPWs resulted in a 2-fold increase in the cell number compared to the low dose. Neovascularization and new bone formation within the ESPW-thickened periosteium was evident after 4 days.

The newly formed bone in this study example and previous reports of periosteal osteogenesis illustrate the potential of ESPW for bone tissue engineering. The results support the proposition that ESPW could be employed as a noninvasive technique to induce cambium layer 10 proliferation prior to the intraoperative harvesting of the periosteum as an autograft or as a source of progenitor cells for tissue engineering applications.

According to embodiments of the invention, periosteal cells as progenitor cells for both cartilagenous & osseous tissue may be clinically harvested at time of surgery and implanted in defect site. An outpatient, noninvasive application of shock waves may thicken periosteum for further clinical applications.

Figure 3:
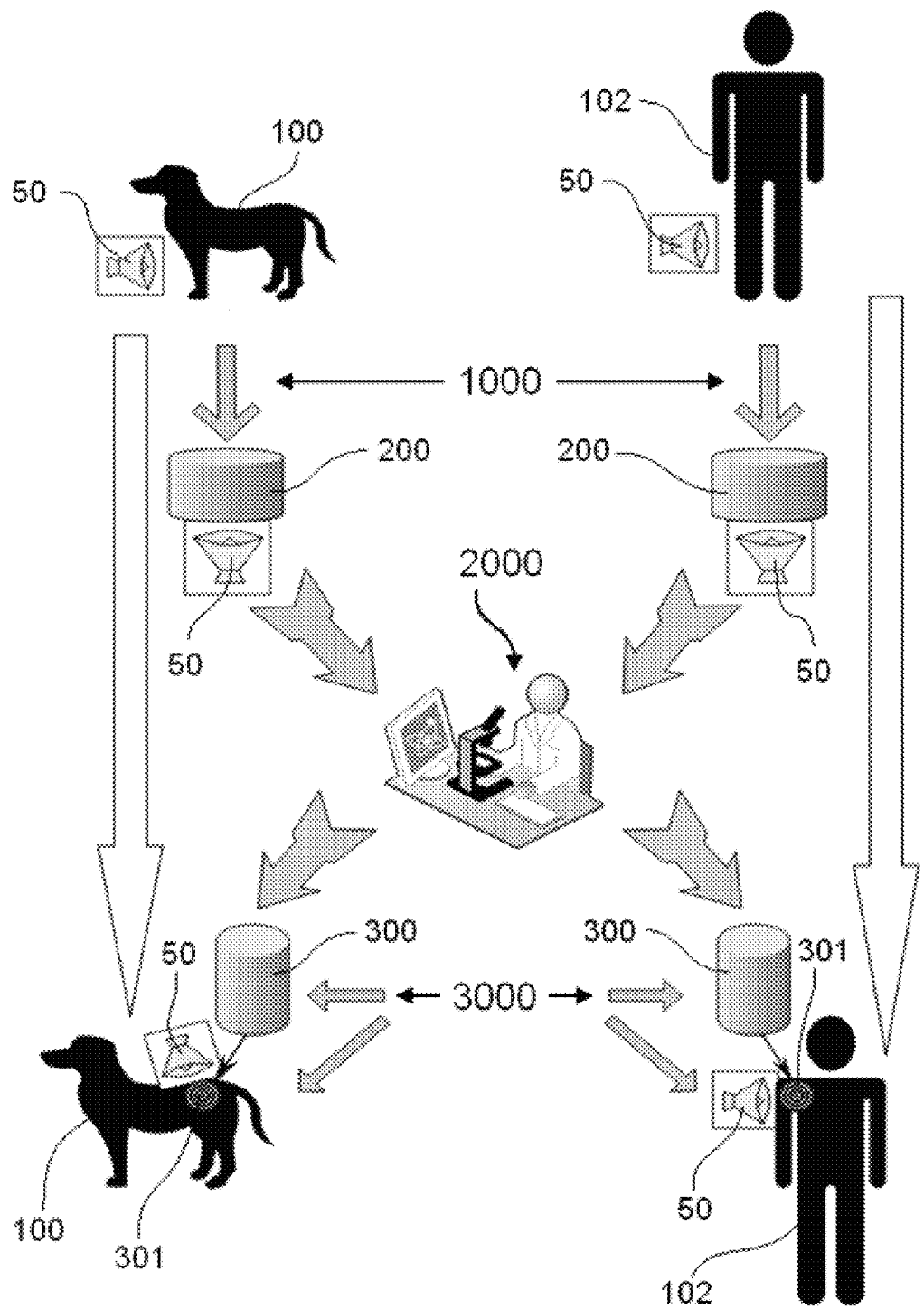
FIG. 3 is a schematic relational process diagram of donor/recipient stem cell proliferation, viability assessment and differentiation steps in a transplant process according to one embodiment of the present invention.

Referring to FIG. 3, stem cell proliferation step 1000, stem cell assessment step 2000 and stem cell differentiation step 3000 may be utilized with shock wave application in various therapeutic methods of the invention. Pressure/shock waves can be used not only to stimulate adult stem cells in-vivo for harvesting purpose, as well to stimulate in-vitro proliferation of stem cells cultures for embryonic stem cells, adult stem cells or induced pluripotent stem cells. The use of shock waves presents a faster and cheaper method to conventional technologies to stimulate enough stem cells for implantation (step 3000).

Proliferation Step

In one embodiment of proliferation step 1000 shock waves from applicator 50 may be applied to a human 102 or to an animal 100 stem cell donor, at a stem cell target site used to proliferate stem cells in-vivo. Alternatively, or as a complement to harvested, proliferated stem cells, shock waves from an applicator 50 may be applied in-vitro to stem cells in culture 200 to proliferate the stem cells. In other embodiments, stem cells proliferated from an animal donor 100 and/or human donor 102 may be harvested and implanted without an intermediary culture 200.

Assessment

At assessment step 2000, stem cells proliferated by in-vivo and/or in-vitro shock wave application are assessed for viability in embodiments of the invention. Based on positive assessment, in further embodiments, the stem cells are differentiated in step 3000. before implantation.

Differentiation Step

One of the fundamental properties of stem cell is that it does not have any tissue-specific structures that allow it to perform specialized functions. However, unspecialized stem cells can give rise to specialized cells, including heart muscle cells, blood cells, or nerve cells. When unspecialized stem cells give rise to specialized cells, the process is called differentiation as shown at step 3000. Signals inside and outside cells can trigger each stem cell to the differentiation process. The internal signals are controlled by cell's genes that carry coded instructions for all cellular structures and functions.

The external signals for cell differentiation include chemicals secreted by other cells, physical contact with neighboring cells, certain molecules in the microenvironment and mechanical stress (as can be done using pressure waves).

The stem cells 300 that are ready for differentiation in general being non-differentiated, in order to be used for a certain treatment, undergo a normal differentiation pathway as follows:

- Hematopoietic stem cells give rise to all the types of blood cells as red blood cells, B lymphocytes, T lymphocytes, natural killer cells, neutrophils, basophils, eosinophils, monocytes, and macrophages;
- Mesenchymal stem cells give rise to a variety of cell types as bone cells (osteocytes), cartilage cells (chondrocytes), fat cells (adipocytes), and other kinds of connective tissue cells such as those in tendons;
- Neural stem cells in the brain give rise to its three major cell types as nerve cells (neurons) and two categories of non-neuronal cells—astrocytes and oligodendrocytes;
- Epithelial stem cells in the lining of the digestive tract give rise to several cell types as absorptive cells, goblet cells, paneth cells, and enteroendocrine cells;
- Skin stem cells occur in the basal layer of the epidermis and give rise to keratinocytes, which migrate to the surface of the skin and form a protective layer;
- Skin stem cells found at the base of hair follicles can give rise to both the hair follicle and to the epidermis;
- Cambium cells from periosteum give rise to bone cells (osteocytes) and cartilage cells (chondrocytes); and
- Embryonic stem cells (ES) and induced pluripotent stem cells (iPSCs) theoretically can differentiate in any of the 200 cell types of the adult body.

Embryonic stem cells, being pluripotent cells, require specific signals for correct differentiation, if injected directly into another body. Also, the cells must be able to avoid the problem of immune rejection.

Because adult stem cells can be obtained from the intended recipient (an auto graft) the risk of rejection is typically non-existent. Thus, adult stem cells and pluripotent stem cells (iPSCs) can generate tissues that are less likely to initiate rejection by the immune system after transplantation, which can avoid continuous administration of immunosuppressive drugs that may cause deleterious side effects. This is possible because the patient's own cells could be expanded in culture, coaxed into assuming a specific cell type (differentiation), and then reintroduced into the patient without immune rejection.

Pressure/shock waves can be used in embodiments not only to stimulate adult stem cells in-vivo for harvesting purpose, or to stimulate in-vitro proliferation of stem cells cultures for embryonic stem cells, adult stem cells or induced pluripotent stem cells, but also for differentiation of the stem cells in the desired type of tissue before the implantation.

After implantation, the object of the stem cells 300 is to create new viable tissue, which has full functionality and avoids rejection. Extracorporeal or intracorporeal pressure/shock waves may be used in embodiments of this stage of cell therapy with advantages as follows:

1) Stimulation of the stem cell therapy targeted tissue for new blood vessels generation 4 to 24 hours before stem cells implantation or repeated sessions, including but not limited to embodiments of at 5, 3 and 1 day before implantation. In this way new pathways may be created to bring nutrients via blood in the implantation zone, which can increase the survival rate of the implanted stem cells and therefore producing faster and better clinical results of the stem cells therapy;

2) In-vivo stimulation with a shock applicator 50 immediately after stem cells implantation to a recipient site 301 increase viability and survival in the implantation area; and 3) Sustaining promotion of new blood vessels and other growth factors combined with in-vivo survival and viability of the stem cells. In some embodiments up to several weeks or months of pressure wave applications may be provided after implantation. In one embodiment, for approximately two weeks after implantation, pressure wave treatments may be provided, such as, but not limited to from two to about 4 treatments, in one or more combinations of from every day up to every three days during the post-implantation period.

In summary, the pressure/shock waves can be used in embodiments of the invention to stimulate adult stem cells in-vivo for harvesting purpose, to stimulate in-vitro proliferation of stem cells cultures, to produce differentiation of the stem cells in the desired type of tissue before implantation or after implantation, to prepare the implantation bed before stem cells treatment and finally to sustain the viability of the stem cells and integration into viable tissue after implantation. Embodiments of the invention may be applied to all types of stem cells—embryonic stem cells, adult stem cells or induced pluripotent stem cells.

The adult stem cells origin can be the brain, bone marrow, peripheral blood, blood vessels, menstrual blood, skeletal muscle, skin, teeth, heart, gut, liver, ovarian epithelium, bone, umbilical vein endothelial cells, fat and testis or any other tissue that can provide sufficient number of stem cells for harvesting.

Pressure/shock wave propagation generates high compressive forces and also cavitation. For the cell culture and differentiation steps based on the sensitivity of each specific stem cell line, the cells can be exposed selectively to either compressive forces plus cavitation or mainly to compressive forces. For specific cases, cavitation can be suppressed using pressurized enclosures for stem cells culture in addition to normal settings used for pressure/shock waves generating devices. In embodiments, the ambient cavitation suppression pressure of the stem cells in a pressurized container may be approximately 1 to 3 bars and used in conjunction with application of pressure waves to the stem cells. The same enclosures can be saturated with specific gases, drugs in vaporized form, and the like, to increase viability of the cells.

Pressure/shock waves can be used for one, some or all the main steps of the stem cells treatments as presented in FIG. 3. In some embodiments, a combinatorial process of proliferation and transplant (autologous and allogenic) using pressure waves in the invention may be made with or without culturing and viability assessment. In other embodiments, the pressure/shock wave treatment can be applied to only specific steps, such as to the stimulation step before harvesting, to the cell culture step, to the differentiation step, to the implantation step and post-implantation step. Finally for each individual customized stem cell treatment the pressure/shock waves can be applied to unique combination of the steps presented before.

The stem cells stimulated with the pressure/shock waves can be harvested, multiplied in the culture and finally introduced into the same donor from where the stem cells were harvested or can be implanted in another subject. Also, in cases when the donor of the stem cells is not the receiving patient, to avoid rejection the stem cell culture can be combined with delivery of anti-rejection drugs that can be localized delivered using the same pressure/shock wave that were delivered for stem cells stimulation and survival after implantation.

For preservation and transport the stem cells lines are usually frozen and for use at the destination they are de-frozen and brought to an active state. In some embodiments, pressure shock waves can provide a more efficient manner to stimulate such cells and can shorten the time for revival. Also, the pressure/shock wave treatment can create a more predictable proliferation of the cell cultures due to discrete simulation with the same amount of energy before or after culture transfer.

It is also possible to use the pressure/shock wave to stimulate and differentiate stem cells cultures in complete tissues or organs that can be used as implants for organ failures, reconstructive surgery, cosmetic surgery, and the like.

Each step of the stem cell's treatment process may utilize different settings as subsequently described.

The in-vivo pressure/shock wave treatment used to enhance adult stem cells proliferation and thus allowing harvesting of sufficient number of cells to be used later for implantation the following settings can be used in embodiments:

For soft tissues, including bone marrow: from about 250 to about 1000 pulses, and in one preferred embodiment from about 250 to about 500 pulses; for soft tissues, including bone marrow: energy flux densities from about 0.1-0.4 mJ/mm$^2$, and in one preferred embodiment energy flux densities of about 0.15-0.23 mJ/mm$^2$ and frequency of delivering pulses of 1-8 Hz.

For hard tissues: from about 1,000 to about 5,000 pulses, and in one preferred embodiment about 3000 pulses/one session or 3 sessions of about 1000 pulses; for hard tissue: energy flux densities from about 0.1-1.0 mJ/mm$^2$, and in one preferred embodiment energy flux densities of about 0.15-0.42 mJ/mm$^2$; and frequency of delivering pulses of 1-8 Hz.

The in-vitro pressure/shock wave treatment used to stimulate stem cells to proliferate in culture can be used before and/or after each culture transfer and includes the following settings in embodiments of the invention: about 200-1000 pulses, and about 250-500 pulses in one preferred embodiment; energy flux densities of about 0.1-0.3 mJ/mm$^2$, and in one preferred embodiment energy flux densities of about 0.15-0.19 mJ/mm$^2$; and frequency of delivering pulses of 1-8 Hz.

The in-vitro pressure/shock wave treatment used to differentiate the stem culture in specific tissue according to the following settings in embodiments of the invention in pressurized and unpressurized enclosures (one time treatment): about 250-1000 pulses, and about 500 pulses in one preferred embodiment; energy flux densities of about 0.1 to 1.0 mJ/mm$^2$, and in one preferred embodiment energy flux densities of about 0.14-0.23 mJ/mm$^2$; and frequency of delivering pulses of 1-8 Hz.

The in-vivo pressure/shock wave treatment used to prep the implantation bed (one treatment 24 hours before implantation or repeated sessions, such as but not limited to at 5, 3 and 1 day before implantation) includes in embodiments: about 100-5000 pulses, and in one preferred embodiment about 500-5000 pulses (depending on treatment area); energy flux densities of about 0.1 to 1.0 mJ/mm$^2$, and in one preferred embodiment energy flux densities of about 0.1-0.3 mJ/mm$^2$; and frequency of delivering pulses of 1-8 Hz.

The in-vivo pressure/shock wave treatment used to differentiate the stem cells into specific tissue and survival after implantation includes the following settings (multiple treatments, one each day or every other day for two weeks) in embodiments: about 100-1000 pulses, and in one preferred embodiment about 200-400 pulses; energy flux densities of about 0.01 to 0.4 mJ/mm$^2$, and in one preferred embodiment energy flux densities of about 0.05-0.15 mJ/mm$^2$; and frequency of delivering pulses of 1-8 Hz.

Non-limiting examples of application of stem cells stimulated by the pressure/shock wave in different stages for improved efficiency and viability at cellular, tissue and organ levels include: implants for organ and tissue failure; periodontal/oral/maxillofacial surgery; nerve regeneration; eliminate cardiovascular ischemia; orthopaedic surgery; plastic surgery; tissue or organ growth (e.g. for transplants); tissue engineering; soft tissue filling; hard tissue/bone filling; cardiovascular defects, disorders and conditions; tissue infarction; tissue ischemia; therapies; injuries; organism fluids; diseases and pathological conditions; autoimmune disorders; and genetic defects.

While the invention has been described with reference to exemplary structures and methods in embodiments, the invention is not intended to be limited thereto, but to extend to modifications and improvements within the scope of equivalence of such claims to the invention.

What is claimed is:

1. A method comprising:
    applying to in-vivo stem cells at a first target location in a human or animal body a first number of shock waves to proliferate stems cells as in-vivo proliferated stem cells in place at the first target location;
    after applying the first number of shock waves, harvesting at least some of the in-vivo proliferated stem cells as harvested stem cells from the target first location;
    after harvesting at least some of the in-vivo proliferated stem cells, applying to at least some of the harvested stem cells in-vitro a second number of shock waves to further proliferate the harvested stem cells as in-vitro proliferated stem cells;
    applying to a second target location in a human or animal body a third number of shock waves to stimulate blood vessel formation at the second target location;
    after applying the second number of shock waves and the third number of shock waves, transplanting by at least one of autologous transplant and allogenic transplant at least some of the in-vitro proliferated stem cells as transplanted stem cells to the second target location for treatment; and
    after transplanting at least some of the in-vitro proliferated stem cells, applying to at least some of the transplanted stem cells at the second location a fourth number of shock waves to stimulate reconstruction of tissue at the second target location.

2. The method of claim 1, wherein the in-vivo stem cells at the first target location are selected from the group consisting of somatic stem cells and induced pluripotent stem cells.

3. The method of claim 1, wherein the first number of shock waves is between 250 pulses and 1000 pulses;
    wherein the pulses are applied at a frequency between 1 Hz and 8 Hz; and
    wherein the pulses have an energy flux density between 0.1 mJ/mm$^2$ and 1.0 mJ/mm$^2$.

4. The method of claim 1, wherein the first number of shock waves is between 1,000 pulses and 5,000 pulses;
    wherein the pulses are applied at a frequency between 1 Hz and 8 Hz; and
    wherein the pulses have an energy flux density between 0.1 mJ/mm$^2$ and 1.0 mJ/mm$^2$.

5. The method of claim 1, wherein the second number of shock waves is between 200 pulses and 1000 pulses;
    wherein the pulses are applied at a frequency between 1 Hz and 8 Hz; and wherein the pulses have an energy flux density between 0.1 mJ/mm² and 0.3 mJ/mm².

6. The method of claim 1, wherein the third number of shock waves is between 100 pulses and 5000 pulses;
wherein the pulses are applied at a frequency between 1 Hz and 8 Hz; and
wherein the pulses have an energy flux density between 0.1 mJ/mm² and 1.0 mJ/mm².

7. The method of claim 1, wherein the fourth number of shock waves is between 100 pulses and 1000 pulses;
wherein the pulses are applied at a frequency between 1 Hz and 8 Hz; and
wherein the pulses have an energy flux density between 0.1 mJ/mm² and 0.4 mJ/mm².

8. The method of claim 1, wherein the first target location is the cambium layer of a bone in a human or animal body.

9. The method of claim 1, further comprising:
after harvesting at least some of the in-vivo proliferated stem cells, placing the harvested stem cells into an interior of a sealed container; and
applying between 1 bar and 3 bars of pressure to the interior of the sealed container during application of the second number of shock waves.

10. The method of claim 1, wherein the applying to a second target location a third number of shock waves to stimulate blood vessel formation at the second target location occurs between 4 hours and 5 days prior to the transplanting.

11. A method comprising:
applying to in-vivo stem cells at a first target location in a human or animal body a first number of shock waves to proliferate stems cells as in-vivo proliferated stem cells in place at the first target location;
wherein the first number of shock waves is between 250 pulses and 5000 pulses, the pulses are applied at a frequency between 1 Hz and 8 Hz, and the pulses have an energy flux density between 0.15 mJ/mm² and 0.42 mJ/mm²;
after applying the first number of shock waves, harvesting at least some of the in-vivo proliferated stem cells as harvested stem cells from the target first location;
after harvesting at least some of the in-vivo proliferated stem cells, applying to at least some of the harvested stem cells in-vitro a second number of shock waves to further proliferate the harvested stem cells as in-vitro proliferated stem cells;
wherein the second number of shock waves is between 250 pulses and 500 pulses, the pulses are applied at a frequency between 1 Hz and 8 Hz, and the pulses have an energy flux density between 0.15 mJ/mm² and 0.19 mJ/mm²;
applying to a second target location in a human or animal body a third number of shock waves to stimulate blood vessel formation at the second target location;
wherein the third number of shock waves is between 500 pulses and 5000 pulse, the pulses are applied at a frequency between 1 Hz and 8 Hz, and the pulses have an energy flux density between 0.1 mJ/mm² and 0.3 mJ/mm²;
after applying the second number of shock waves and the third number of shock waves, transplanting by at least one of autologous transplant and allogenic transplant at least some of the in-vitro proliferated stem cells as transplanted stem cells to the second target location for treatment; and
after transplanting at least some of the in-vitro proliferated stem cells, applying to at least some of the transplanted stem cells at the second location a fourth number of shock waves to stimulate reconstruction of tissue at the second target location;
wherein the fourth number of shock waves is between 200 pulses and 400 pulses, the pulses are applied at a frequency between 1 Hz and 8 Hz, and the pulses have an energy flux density between 0.05 mJ/mm² and 0.15 mJ/mm².

12. The method of claim 11, wherein the first target location is the cambium layer of a bone in a human or animal body.

13. The method of claim 11, wherein the in-vivo stem cells at the first target location are selected from the group consisting of somatic stem cells and induced pluripotent stem cells.

14. The method of claim 11, further comprising:
after harvesting at least some of the in-vivo proliferated stem cells, placing the harvested stem cells into an interior of a sealed container; and
applying between 1 bar and 3 bars of pressure to the interior of the sealed container during application of the second number of shock waves.

* * * * *